United States Patent [19]

Mori

[11] Patent Number: 4,799,629
[45] Date of Patent: Jan. 24, 1989

[54] FLYING OBJECT FOR COLLECTING SOLAR RAYS

[76] Inventor: Kei Mori, 3-16-3-501, Kaminoge, Setagaya-ku, Tokyo, Japan

[21] Appl. No.: 119,364

[22] Filed: Nov. 10, 1987

[30] Foreign Application Priority Data

Dec. 8, 1986 [JP] Japan .............................. 61-292148

[51] Int. Cl.[4] .............................................. B64B 1/24
[52] U.S. Cl. ..................................... 244/23 C; 244/26; 244/30; 244/5
[58] Field of Search ....................... 244/30, 31, 24, 26, 244/29, 23 C, 5; 126/425, 438, 439, 440

[56] References Cited

U.S. PATENT DOCUMENTS 4,326,681  4/1982  Eshoo .................................... 244/30
4,484,565  11/1984  Mori .................................... 126/425
4,534,525  8/1985  Bliamptis ............................ 244/30

Primary Examiner—Joseph F. Peters, Jr.
Assistant Examiner—Rodney Corl
Attorney, Agent, or Firm—Jordan & Hamburg

[57] ABSTRACT

A flying object for collecting solar rays comprises a disk-shaped flying body equipped with floating and propelling means installed at the outer circumferential portions thereof. The flying object can detect its direction of flight and keep its position constant by means of the plural floating and propelling means. In addition, the flying object has a solar ray collecting device, equipped with solar ray collecting lenses. The solar rays collected by the solar ray collecting device are guided through an optical conductor cable into the flying object.

2 Claims, 3 Drawing Sheets

4,799,629

FLYING OBJECT FOR COLLECTING SOLAR RAYS

BACKGROUND OF THE INVENTION

The present invention relates to a flying object for collecting solar rays and which carries a solar ray collecting device for the purpose of administering medical treatment, doing experiments, or for other like purposes.

An automatic solar ray collecting device previously proposed by the present applicant has a cylindrical foundation and a transparent dome-shaped head portion. A capsule of the solar ray collecting device is constructed with the foundation and the head portion. As to the employment of the device, a solar ray collecting assembly device is accommodated in the capsule.

The solar ray collecting assembly device comprises a large number of optical lenses (for instance, nineteen lenses) for focusing the sun's ray, a light ray direction sensor for sensing the direction of the sun, a support frame for unitarily folding the lenses and the sensor, a first motor for rotating those elements with a rotatable shaft (horizontally arranged shaft), a support arm for supporting the afore-mentioned elements from the lenses to the motor, another rotatable shaft disposed (vertically arranged shaft) so as to intersect the rotatable shaft of the afore-mentioned motor perpendicularly thereto, and a second motor for rotating the rotatable shaft (vertically arranged shaft). The direction of the sun is sensed by the afore-mentioned light ray direction sensor. The first and second motors are controlled by means of control devices so as to always direct the lenses toward the sun. The light-receiving end of the optical conductor cable is placed at the focal position of the lenses. The light rays are guided into the optical conductor cable and transmitted therethrough onto the optional desired place.

The present applicant has also proposed a solar ray radiation device for use in medical treatment, in which only the visible light rays, not containing ultraviolet or infrared rays, are guided into the optical conductor cable, by adjusting the position of the light-receiving end of the optical conductor cable disposed on the focal position of the lenses, in such a manner as mentioned above, and the visible light rays are radiated onto the organization of a living body in order to promote a the living body reaction or prevent the skin of a human body from growing old, and further, in order to cure the human body from arthritis, neuralgia, bedsores, rheumatism, burns, skin disease, injuries, bone fractures, or the like, and to stop pain from those diseases.

However, although the above-mentioned solar ray radiation device for use in medical treatment utilizes the beneficial light energy of the sun's rays, and further more the physiological function of the visible light rays contained in solar rays can be utilized for administering medical treatment and for preventing various diseases related to the field of medical science and the usefulness of the same in the advanced fields of agricultural technology and biotechnology. A serious problem arises in relation to the weather conditions at the installation site because of utilizing the sun's rays i.e. solar ray energy can't effectively be utilized during bad weather because the sun's rays are blocked by a cloud cover.

SUMMARY OF THE INVENTION

The primary object of the present invention is to provide a flying object for collecting the sun's rays which is equipped with a solar ray collecting device.

Another object of the present invention is to provide a flying object which rises up above the cloud cover and achieves the environmental conditions necessary for collecting the sun's rays.

It is another object of the present invention to provide a flying object equipped with an auxiliary floating means, it may be possible to float the flying object in the air at high altitudes for a long periods of time and of consuming small amounts of fuel.

It is another object of the present invention to provide a flying object wherein patient suffering from diseases such as arthritis can be radiated by the sun's rays regardless of the weather condition on the ground.

DESCRIPTION OF THE PREFERRED EMBODIMENTS

Figure 1:
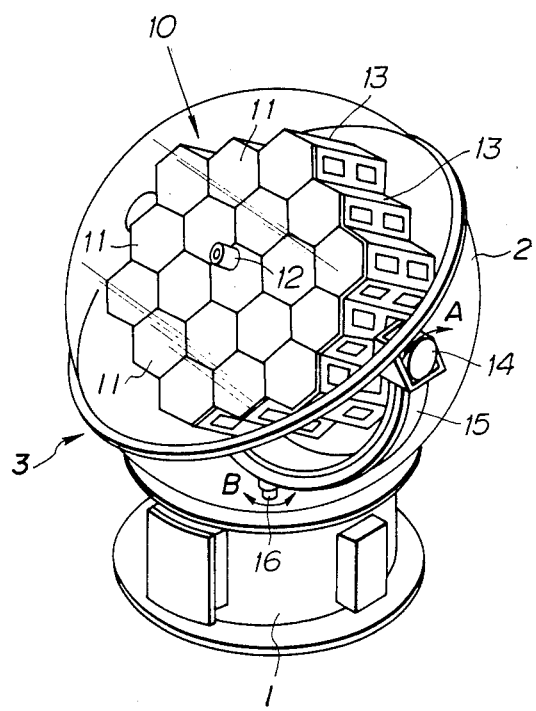
FIG. 1 is a perspective view showing the outline of the solar ray collecting device.
Figure 4:
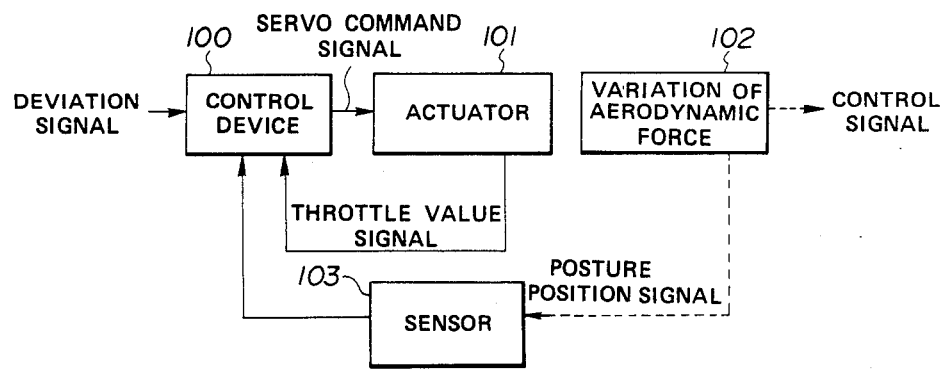
FIG. 4 is a block diagram of the control system for controlling the flying object according to the present invention.

FIG. 1 is a perspective view for explaining the embodiment of a capsule employed with the solar ray collecting device which had been previously proposed by the present applicant. In FIG. 1, 1 is a cylindrical base portion, 2 is a transparent dome-shaped head portion, and a capsule, 3 employed with the solar ray collecting device, is constructed of base portion 1 and head portion 2. A solar ray collecting device 10 is accommodated in the capsule 3, as shown in FIG. 4, at the time of employing the device 10.

The solar ray collecting device 10 comprises a large number of lenses (for instance, nineteen lenses) 11 for focusing the sun's rays, a direction sensor 12 for sensing the direction of the sun, a supporting frame 13 for unitarily supporting those lenses 11 and the sensor 12, a first motor 14 for rotating those elements in the direction shown by arrow A, a holding arm 15 for holding the afore-mentioned lenses 11 onto the motor 14, a rotatable shaft 16, disposed so as to intersect perpendicularly to the rotatable shaft of the motor 14, and a second motor (not shown in FIG. 1) for rotating the rotatable shaft 16 in the direction shown by arrow B.

The direction of the sun is detected by the sensor 12, and its detection signal controls the afore-mentioned first and second motors so as to direct the lenses 11 toward the sun. The solar rays focused by the lenses 11 are guided into an optical conductor cable not shown in FIG. 1, the light-receiving end of which is disposed on the focal position of the lenses 11. The guided solar rays are transmitted through the optional conductor cable to the optical desired place.

The present applicant has also proposed a solar ray radiation device for use in medical treatment, in which only the visible light rays, not containing ultraviolet or infrared rays, are guided into the optical conductor cable, by adjusting the position of the light-receiving end of the optical conductor cable disposed on the focal position of the lenses, in such a manner as mentioned above, and the visible light rays are radiated onto the organization of a living body in order to promote a the living body reaction or prevent the skin of a human body from growing old, and further, in order to cure the human body from arthritis, neuralgia, bedsores, rheumatism, burns, skin disease, injuries, bone fractures, or the like, and to stop pain from those diseases.

However, although the above-mentioned solar ray radiation device for use in medical treatment utilizes the beneficial light energy of the sun's rays, and furthermore, the physiological function of the visible light rays contained in solar rays can be utilized for administering medical treatment and for preventing various diseases related to the field of medical science and the usefulness of the same in the advanced fields of agricultural technology and biotechnology. A serious problem arises in relation to the weather conditions at the installation site because of utilizing the sun's rays i.e. solar ray energy can't effectively be utilized during bad weather because the sun's rays are blocked by a cloud cover.

Figure 2:
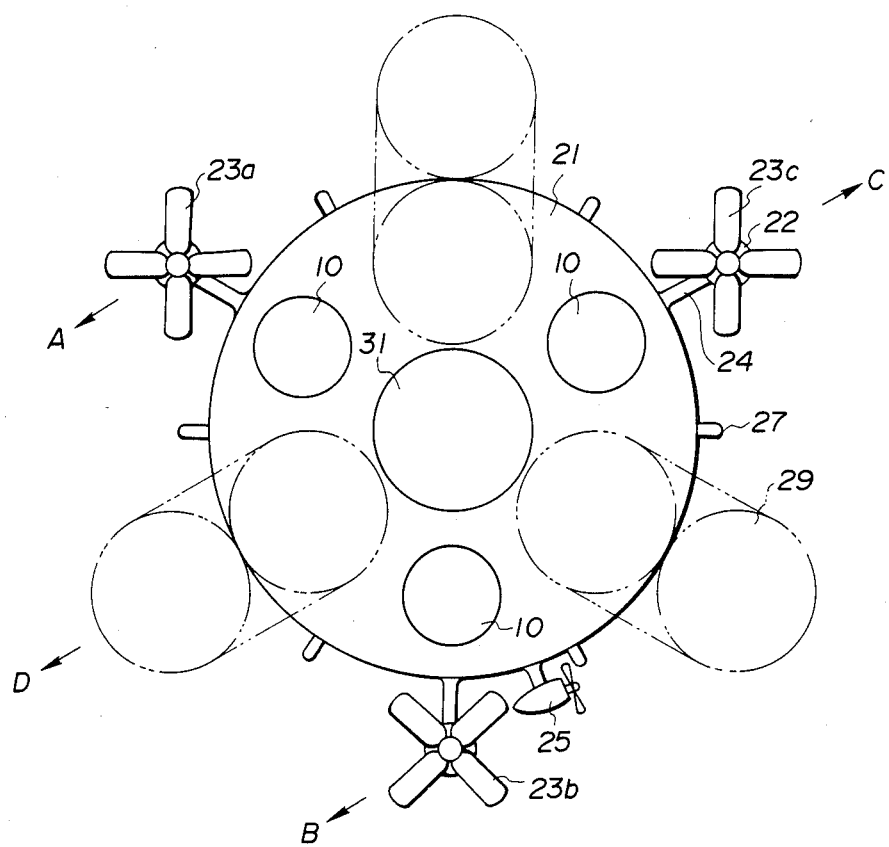
FIG. 2 is a plane view for showing an outline of the flying object used for collecting solar rays according to the present invention.
Figure 3:
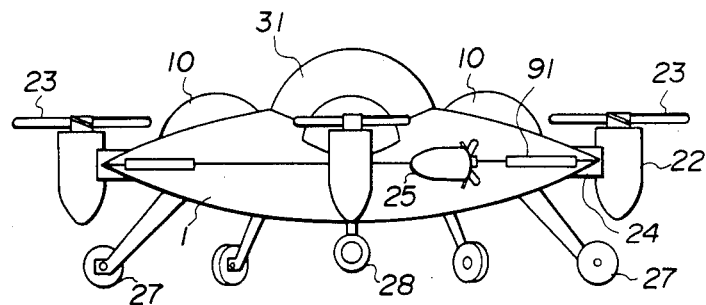
FIG. 3 is a side view for explaining the same.

FIG. 2 is a plane view for explaining the outline of a flying object for collecting solar rays according to the present invention, and FIG. 3 is a side view for explaining the same. In FIG. 2 and 3, 21 is a machine portion thereof. For instance, the machine 21 is made as a measurement-gauge with little air-resistance resistance and made of synthetic resin compound material and formed in the shape of flat disk with a mono-cock construction. On the outer circumference of the machine 21, there are installed a plurality of floating and propelling means consisting of an engine 22 and a propeller 23 through the intermediary of arms 24, wherein the driving shaft of the respective engines 22 and propellers 23 is capable of rotating (changing the direction thereof) in connection with the machine's surface. (hereinafter, the propeller is shown by the reference numeral 23 related to 23a, 23b and 23c.) When the flying object rises up, the propeller 23 is parallel with the surface of the machine 21 as shown in FIG. 3. Therefore, the flying object can be lifted up in a vertical direction by the action of the propeller 23. When the propeller 23 rotates to change the direction of its surface, a horizontal component force is produced so that the flying object can move in a horizontal direction. For instance, as shown in FIG. 2, if the propeller 23a is directed in the direction shown by arrow A, the propeller 23b in direction B, and the propeller 23c in direction C, and further the propeller 23c is rotated in a direction opposite to that of the propellers 23a and 23b, the flying object can move in a direction shown by arrow D.

The flight velocity of the flying object can be determined by changing the horizontal component force of the propeller 23 in such a way, and a propelling jet 28 is installed on the lower surface of the flying object's machine 21 in a horizontal direction for the purpose of increasing the flight velocity of the flying object. And further, since the rotational movement of the machine 21, having a motion quantity balancing with the generation of the rotational movement accompanying the rotation of the propeller 23 appears, a propelling mechanism 25 for stabilizing the flying object's rotation which generates a rotational torque corresponding to the rotational motion quantity of the machine 21 is installed on the outer circumference of the machine 21 so as to generate a propelling force in the direction of its outer circumference. In the case where the number of floating and propelling means is plural, the balanced condition of the rotational movement of the machine 21 is kept by reversing the rotational direction of the propeller 23. Therefore, it may be sufficient to utilize a rotation-stabilizing, propelling mechanism 25 of small capacity. Although the above-mentioned floating and propelling means employs a propeller 23, it may be possible to employ a jet-propelled type mechanism in a similar way. In FIG. 2, 27 is a leg. A plurality of legs 27 are attached to the machine 21 at uniform intervals along the circumferential direction thereof. When the flying object is lifted up, the legs 27 are retracted into the machine 21.

According to the present invention, solar ray collecting devices 10 are arranged at almost equal intervals on the upper surface of the flying object as mentioned above. The effective wave-length component, for instance, the visible light ray components of the sun's rays, collected by the use of the solar ray collecting devices 10, is transmitted through an optical conductor cable onto the light ray radiation means set up in the machine 21. The light rays transmitted in such a way are radiated onto the targeted object, as for instance, the skin's surface (or a patient) by the use of the light ray radiation means. The flying object is lifted up into the air to a high-altitude where the solar rays are not interrupted by the clouds, by the means of the propeller 23, the propelling jet 28, or the like, and thereby the light radiation can be effectively performed in the flying object. With respect to floating of the flying object, it may be desirable that each floating means interact in balanced conditions and support the machine 21 horizontally in order to maintain a stable posture. As a result, the controlled amount, such as the rotation number of the engine, the direction thereof, or the like has to be controlled in relation to the targeted area at the time of actualizing a horizontal flight, for the purpose of obtaining such control.

FIG. 4 is a block diagram showing an embodiment of a control system for controlling the flying object as mentioned above. In FIG. 4, the block diagram consists of a control device 100, an actuator 101, a variation amount of the machine's aerodynamic force 102, and a sensor 103. In case that the floating forces created by the respective floating means 22 and 23 are not uniform at the time of floating (horizontally), the water level (horizontal) shaft of the flying object's machine 21 creates a rotational movement against the ground surface. Such rotation is in-put, for instance, to the sensor 103 such as a gyro-compass or the like as a rotational force, and then, the rotational force becomes output as a precession rotational force signal of the gyro-compass. In such a way, the deviation signal of the horizontal position is applied to the control device 100 and a servo command signal is applied to the actuator 101 for driving the throttle valve, etc. of the engine 22. (In the case of FIGS. 2 and 3, since three engines are provided, three throttle valves are also provided in the flying object.) The engine 22 is driven by the throttle valve driven on the basis of the servo command signal. The variation amount 102 of the aerodynamic force, characteristic of the machine 21, generated as a result of driving the engine 22, is detected by the sensor 103 as a posture position signal of the machine 21. The detected signal is applied to the control device 100. In such a way, a control loop is formed so as to change the degree of opening of the throttle valve.

Moreover, in the case of the horizontal flight, the flying object is controlled also on the basis of a similar control loop. When the flying object floats horizontally and arrives at the target position, a balloon 29 provided in the machine 21 is taken out from the opening 91 for drawing out the balloon 29 into a space outside of the machine 21, and helium gas is sealingly enclosed in the balloon 29 by the use of a liquid helium bomb not shown in FIG. 2 which is set up in the machine 21 and thereby the flying object floats in the air. The balloon 29 as mentioned above, is employed for the purpose of reducing the amount of fuel consumed in the engine 22. Long-periods of floating of the flying object can be realized by employing such a balloon as an auxiliary floating means in place of the engine 22. Furthermore, 31 is a manipulation seat. Thereby solar radiation can be effectively performed in order to attain the aims object of the present invention.

As mentioned above, the flying object according to the present invention is loaded with solar ray collecting devices, and thereby the latter are always situated above the cloud cover so that the solar rays can be effectively collected. And further, since the balloon, sealingly enclosed with helium gas, is employed as an auxiliary floating means, it may be possible to float the flying object in the air at high attitudes for a long periods of time and of consuming small amounts of fuel. Especially, patient suffering from diseases such as arthritis, can be taken up into the air at high altitudes and the sun's rays can be radiated onto the patient effectively. On the ground, solar radiation cannot be performed when it is cloudy or rainy. However, it can always be done in the air at high altitudes regardless of the weather condition.

I claim:

1. A flying object for collecting solar rays and for treatment of personnel in said flying object with said collected solar rays comprising a generally disk-shaped flying body having an interior compartment, said flying body having an outer circumference, propelling means mounted on said body and extending outwardly of said outer circumference, said propelling means being operable to propel said flying object in a desired direction of flight and to maintain said flying object in a fixed airborne position, float means mounted on said body and operable to be deployed to impart a lifting force to said flying object, and solar ray collecting means mounted on said body for collecting solar rays and directing said collected solar rays into said compartment for effecting medical treatment of personnel within said compartment, whereby said flying object is operable to provide said medical treatment by being deployed airborne to an altitude above weather conditions which block solar rays to the earth's surface.

2. A flying object according to claim 1, wherein said float means comprises float storage means on said body, balloon means stored in said float storage means, and helium supply means for supplying helium to said balloon means, whereby said balloon means are operable to be deployed from said float storage means and filled with helium after said flying object has been airborne to thereby provide a lifting force for the flying object.

* * * * *